United States Patent
Suzuki et al.

(10) Patent No.: US 6,372,266 B1
(45) Date of Patent: Apr. 16, 2002

(54) MEDICINAL COMPOSITION FOR TREATING DYSMENORRHEA AND ENDOMETRIOSIS INDUSTRIAL USE

(75) Inventors: Nobutaka Suzuki, Kanazawa; Takafumi Kohama, Nanao, both of (JP)

(73) Assignees: Tradepia Co. Ltd., Saitama (JP); Horphag Research Limited, St. Peter Port Guernsey (GB)

( * ) Notice: Subject to any disclaimer, the term of this patent is extended or adjusted under 35 U.S.C. 154(b) by 0 days.

(21) Appl. No.: 09/575,329

(22) Filed: May 19, 2000

(30) Foreign Application Priority Data

Oct. 8, 1999 (JP) ............................................. 11-287628

(51) Int. Cl.[7] .................................................. A61K 9/00
(52) U.S. Cl. ........................ 424/725; 424/400; 424/439; 424/464
(58) Field of Search ................. 424/439, 195.15, 424/464, 407, 451, 484, 486, 489, 400, 725; 514/14, 183, 212, 365, 456

(56) References Cited

U.S. PATENT DOCUMENTS

| | | | | |
|---|---|---|---|---|
| 4,410,534 A | * | 10/1983 | Muchowski et al. | 424/263 |
| 5,780,060 A | * | 7/1998 | Levy et al. | 424/489 |
| 5,942,539 A | * | 8/1999 | Hughes, Jr. et al. | 514/456 |
| 6,028,088 A | * | 2/2000 | Pershadsingh et al. | 514/369 |
| 6,113,907 A | * | 9/2000 | Khwaja et al. | 424/195.1 |

FOREIGN PATENT DOCUMENTS

WO   WO 97/36497   10/1997

OTHER PUBLICATIONS

Remington's Pharmaceutical Sciences, 18th Edition, p. 1297 (1990).*

* cited by examiner

Primary Examiner—James M. Spear
Assistant Examiner—Charesse L. Evans
(74) Attorney, Agent, or Firm—Cobrin & Gittes

(57) ABSTRACT

A medicinal composition for treating dysmenorrhea and endometriosis comprising a plant extract and containing proanthocyanidins as an effective component thereof. The composition is provided and administered in the form of soft capsules, tablets, or a powdery or liquid preparation to be used for treating dysmenorrhea and endometriosis.

2 Claims, 1 Drawing Sheet n = an integer of 2 to 10 n = an integer of 2 to 10

MEDICINAL COMPOSITION FOR TREATING DYSMENORRHEA AND ENDOMETRIOSIS INDUSTRIAL USE

FIELD OF THE INVENTION

The present invention relates to a medicinal composition for treating dysmenorrhea and endometriosis, and more particularly to a medicinal composition comprising as its effective component a plant extract containing proanthocyanidins.

BACKGROUND OF THE INVENTION

Dysmenorrhea is characterized by spasmodic symptoms, such as severe lower abdominal pain, lumbago, headache and nausea, which develop at the onset of and during menstruation and which are not attributable to other gynecological diseases (adnexitis, endometriosis, uterine myoma, adenomyosis of the uterus, etc.). The causes include increased presence of prostaglandins in the menstrual fluid and an abrupt increase in the intrauterine pressure caused by the menstrual fluid held in the uterus due to the constriction of os uteri. Dysmenorrhea is treated by oral administration of Voltaren (generic name: dichlofenac sodium) or Sedes (generic name: pyrazolone analgesic, antiinflammatory and antipyretic composition). However, this treatment may temporality alleviate the symptoms but is generally ineffective.

Endometriosis is a disease of ectopic occurrence, growth of endometrium (in the ovary, oviduct and Douglas' cul-de-sac) and the disease causing inflammation at the site and developing severe menstrual pain and lower abdominal pain at times other than the menstrual period. It is also one of the causes of sterility. Although still remaining to be clarified, a causal relation to dioxin has attracted attention in recent years. The disease is most prevalent in the reproductive ages (between ages of about 18 to about 42). Because of its dependence on follicular hormones (estrogens), the disease becomes gradually aggravated in menstruating women and conversely becomes alleviated and disappears postmenopausally with reduced production of estrogens.

PRIOR ART

The Gn-RH therapy is most prevalently used which suppresses the secretion of estrogens from the ovary to diminish the lesion. Also used for other treatment is danazol which is a derivative of an androgen (testosterone) for inhibiting the estrogenic activity of the lesion. These therapies nevertheless frequently involve side effects including the symptoms of ovarian deficiency such as hot flushes and systemic malaise, osteoporosis, edema and obesity, and are not fully useful because even with women up to 40 in age, at least 80% of them have a recurrence of endometriosis 3 to 6 months after the completion of the treatment.

Besides those mentioned above, especially effective medicinals are not known for treating dysmenorrhea and endometriosis and improving the symptoms thereof, and it has long been desired to provide such medicinals.

SUMMARY OF THE INVENTION

We have unexpectedly found that plant extracts containing proanthocyanidins exhibit unprecedented remarkable ameliorating or therapeutic effects on patients with dysmenorrhea and endometriosis. Based on this finding, the present invention provides a medicinal composition comprising as its effective component a plant extract containing proanthocyanidins for treating dysmenorrhea and endometriosis.

According to the present invention, French maritime pine bark extracts are especially effective for treating dysmenorrhea and endometriosis. The invention provides a medicinal composition comprising a French maritime pine bark extract, in the form of soft capsules, tablets, or a liquid or powdery preparation for oral administration. However, the medicinal composition for treating dysmenorrhea and endometriosis of the present invention is not restricted to the French maritime pine bark extract but covers all of plant extracts containing proanthocyanidins, for example, a conifer extract and a grape seed extract.

BRIEF DESCRIPTION OF THE DRAWING

The drawing is a diagram showing the structure of a proanthocyanidin.

DESCRIPTION OF THE PREFERRED EMBODIMENT

Figure 1:
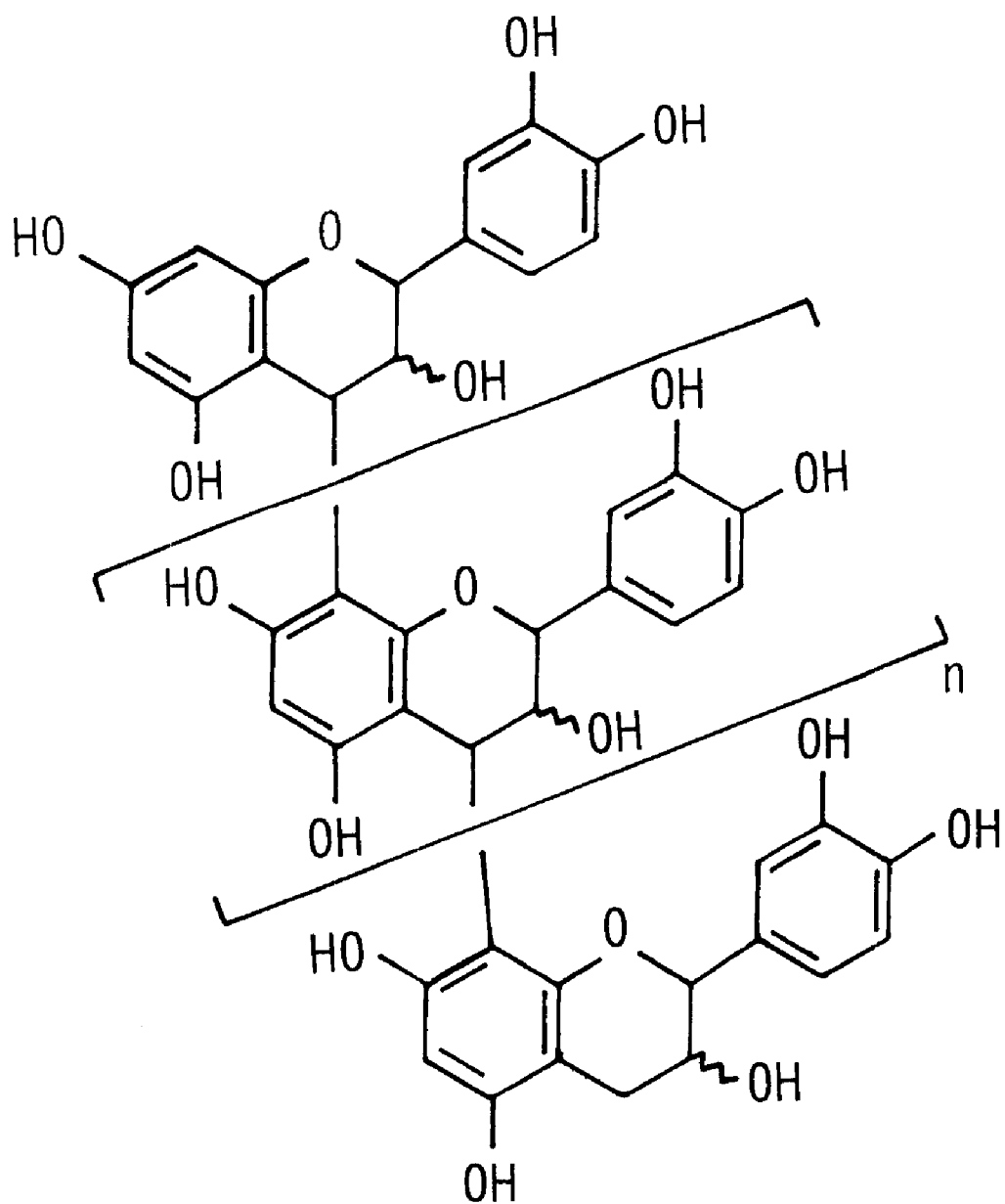

The French maritime pine bark extract is an extract of the bark of a pine botanically called Pinus pinaster (French maritime) and growing on the coast of Bordeaux, France (U.S. Pat. No. 3,436,407). The extract is presently used worldwide as a nutrition supplemental food under the name of Pycnogenol (brand name of Horphag Research, Switzerland). The pharmacological mechanism of the extract involves, for example:

1) intensive antioxidant activity (Blazso, G. Gabor, M., Sibbel, R. and Rohdewald, P. Pharm. Pharmacol. Lett., 3: 217–220. 1994),
2) antiinflammatory activity (ibid.),
3) activity to dilate peripheral blood vessels (Fitzpatrick, D. F., Bing, B. and Rohdewald, P. Jour. Cardiovasc. Pharmacol., 32: 509–515. 1994),
4) ability to prevent platelet aggregation (U.S. Pat. No. 4,698,360),
5) activity to reduce peripheral vascular resistance (Gabor, M. Engi, E. and Sonkodi, S. Phlebologie, 22: 178–182. 1993),
6) activity to reinforce connective tissues (Tixier, J. M., Godeau, G., Robert, A. M. and Hornebeck, W. Biochemical Pharmacology, 33: 3933–3939. 1984), and
7) activity to fortify vitamin C in in vivo activity (Cossins, E., Lee, R. and Packer, L. Biochem. Mol. Biol. Int., 45 (3): 583–597. 1998).

The French maritime pine bark extract further has plant extracts containing proanthocyanidins have a wide variety of pharmacological effects and reportedly produces ameliorating or therapeutic effects including:

1) reduction of cerebral bloodstream disorder in rats (Cahn and M. G. Borzeix, Sem. Hop. Paris, 1983, 59, No. 27–28, 2031–2034),
2) amelioration of peripheral bloodstream disorder due to arteriosclerosis,
3) prevention of thrombosis (U.S. Patent No. 5,720,956),
4) effect to alleviate or remedy ADHD (attention deficient hyperactivity disorder, so-called restless children, hyperactive infants; U.S. Pat. No. 5,719,178),
5) therapeutic effect on diabetic retinopathy (approved as a pharmaceutical in France),
6) aesthetic effect on the skin,
7) analgesic effect,
8) relief or remedy of insomnia,
9) remedy of leg cramps, 10) mitigation or remedy of CFS (chronic fatigue syndrome), and 11) effects on other diseases including swollen leg, varicosis, allergic diseases such as pollinosis and asthma, asthenopia, diabetes and influenza, and prevention of cancers. Further the safety of the extract has been substantiated for the past 30 years by researchers in France, Great Britain, U.S.A., Germany, Italy, etc.

U.S. Pat. No. 3,436,407 discloses in detail as follows an extraction process for obtaining the French maritime pine bark extract, general properties, composition and quantitative determination of the extract.

(1) Extraction Process (U.S. Pat. No. 3,436,407)

A coarse powder (100 kg) of the bark of a French maritime pine is treated in 350 liters of boiled water for 12 hours for extraction, the solid mass is expressed, and the extract and the liquid obtained by expression are collected in a combined amount of 250 liters. The resulting liquid is cooled to 20° C. and filtered. Sodium chloride is added to the filtrate to saturation. The precipitate is filtered off. The filtrate is extracted with ethyl acetate three times, using the acetate in 1/10 of the amount of the aqueous phase each time. The ethyl acetate portions are collected, and the liquid is dried over anhydrous sodium sulfate (NaSO4) and distilled in a vacuum to 1/5 of the initial quantity. The concentrate is then poured into chloroform in 3 times the quantity thereof with physical stirring, permitting proanthocyanidins to precipitate. The precipitate is collected by filtration and dissolved in ethyl acetate again for purification. A precipitate obtained anew from chloroform is eventually washed with chloroform and dried at a temperature of up to 50° C.

(2) General Properties of the Extract

A light beige powder tasting puckery, readily soluble in water and ethyl alcohol, insoluble in $CHCl_3$, $C_4H_6$, petroleum ether and ethyl ether, and preservable in a dry bottle at room temperature for an unlimited period of time. Identification test: When an aqueous solution of the extract as rendered acid with 10% (v/v) hydrochloric acid is heated to the boiling point, the solution turns dark red. When this solution is mixed with isoamyl alcohol with stirring, a supernatant is formed which has the physical and chemical properties of anthocyanidins.

(3) Composition

The French maritime pine bark extract comprises phenolic compounds having an aromatic structure and phenolic group. Polyphenols constituting phenolic compounds are substances having a large molecule and containing phenolic groups. A group of polyphenols provides a proanthocyanidin.

Proanthocyanidins comprise catechin and/or epicatechin units and have a structure shown in the drawing. The drawing shows three hydroxyl groups attached by a wave line, which indicates that the hydroxyl group (OH) can be in a cis or trans arrangement, because proanthocyanidins comprise both catechin and epicatechin, an isomer thereof.

The French maritime pine bark extract contains many kinds of phenolic carboxylic acids including caffeic acid, ferulic acid, p-coumarinic acid and p-benzoic acid, which are all present in plants. Of these acids, some are combined with glucose, forming glucose esters or glucose ethers.

The French maritime pine bark extract has a composition comprising 80 to 85 wt. % of proanthocyanidins, 5 wt. % of catechin and epicatechin, 2 to 4 wt. % of organic acids which include caffeic acid and which are precursors of catechin and epicatechin, up to 8 wt. % of water and the balance impurities.

(4) Quantitative Determination of Proanthocyanidins in the Extract

The proanthocyanidin content of the French maritime pine bark extract is determined utilizing the peculiar affinity of these substances for a collagen. No components of the extract other than proanthocyanidins have similar affinity for the collagen of skins. The bark extract is usable as a substitute for a tannin in a method (wherein a tannin and hide powder are used in combination) recommended in the tanning industry.

Stated more specifically, a specified quantity of the extract is dissolved in water to prepare an aqueous solution of known concentration. The solution is mixed with hide powder, and the mixture is filtered. An aliquot of the filtrate is used to quantitatively determine the solid substances remaining therein. The difference between the concentration of the solution prepared and the concentration of the solid extract corresponds to the combined amount of proanthocyanidins, which remain as such in the hide powder.

Medicinal Composition Used for Treatment

The present invention relates to the use of the plant extract containing proanthocyanidins for treating dysmenorrhea and endometriosis, or to a medicinal composition comprising the extract as its effective component. The active substances provided by the present invention are obtained by subjecting a plant material to extraction according to the following standards.

1) The extract contains proanthocyanidins.

2) The material is available with ease and at a low cost constantly.

3) The extract is free from natural or artificial toxic components.

The bark of conifers, especially pine bark such as French maritime pine bark, is useful as a material of first class. The term the "French maritime pine bark extract" should be understood as meaning the "French maritime pine bark extract containing proanthocyanidins".

The extract is used in the form of an oral preparation or suppository for the absorption of the proanthocyanidins in the alimentary tract. For oral administration, the extract is formulated into tablets, sugar-coated tablets, pellets, pills, capsules, powder wrapped in paper, or contained in vials for use by sucking.

The extract is given at a daily dose of 1.5 to 3 mg per kg of the body weight, calculated as the proanthocyanidin component of the extract. If taken at a dose of less than 1.5 mg, the extract fails to exhibit the effect of proanthocyanidins, whereas if the dose is over 3 mg, an excess of the active component will be discharged from the body uselessly. For example, the dose is 100 to 200 mg/day for male adults weighing 70 kg. It is suitable that the dose to be taken at a time be 50 to 100 mg to assure an active oxygen removal effect.

Used as a food containing the French maritime pine bark extract were a suitable number of soft capsules having enclosed therein a composition comprising 15 mg of the extract, 205 mg of olive oil as an excipient and 30 mg of an emulsifier per capsule (brand name: "Pycnogenol", product of Horphag Research).

Dysmenorrhea (1) Patients

The patients, eight females from 17 to 32 years in age, had a severe lower abdominal pain and lumbago continually at least for the past 6 months during every menstrual period and invariably administered an analgesic (Voltaren, Sedes or the like). The patients were clinically diagnosed by gynecological examination, hematological examination (findings as to inflammation, serum CA-125) and imaging examination (CT scan and MRI) and found to have no other gynecological diseases such as endometriosis and adnexitis.

(2) Method of Administration

The medicinal composition was given to the patients listed in Table 1 by one of three methods A, B and C.

Method A for six patients: 30 mg/day for 14 days from 7 days before menstruation.

Method B for one patient: 30 mg/day continuously for one month.

Method C for one patient: 60 mg/day once.

TABLE 1

Treatment of Dysmenorrhea with the Extract

| Patient | Age | Chief complaint | Diagnosis | Method and period | Improvement |
|---|---|---|---|---|---|
| 1 | 30 | Severe cramp | Dysmenorrhea | A x 1 | Moderate |
| 2 | 23 | Severe cramp | Dysmenorrhea | A x 1 | Marked |
| 3 | 27 | Severe cramp | Dysmenorrhea | A x 3 | No |
| 4 | 32 | Severe cramp | Dysmenorrhea | B x 1 | Marked |
| 5 | 17 | Severe cramp | Dysmenorrhea | A x 1 | Moderate |
| 6 | 21 | Severe cramp | Dysmenorrhea | A x 1 | Moderate |
| 7 | 19 | Severe cramp | Dysmenorrhea | A x 1 | Moderate |
| 8 | 17 | Severe cramp | Dysmenorrhea | C | Moderate |

(3) Result

The medicinal composition was ineffective in only one patient treated by method A for three menstrual periods (effective ratio: 88%). The severe lower abdominal pain and lumbago during the menstrual period disappeared in all the other patients, eliminating the need for analgesics.

Further in three of the improved cases, the menstrual pain mitigated or disappeared during the menstrual periods subsequent to the improvement without administering the extract and the other analgesics so far used.

(4) Evaluation

Dysmenorrhea is treated usually by using analgesics (Voltaren, Sedes, etc.). However, these drugs, if orally administered, are generally unlikely to completely eliminate the menstrual pain; presently most patients can do nothing but bear the pain. The patient is in fear of the severe pain to be experienced during menstruation and becomes mentally unstable not only during the menstrual period but also with the approach of every menstruation, which seriously impairs the quality of life. Not infrequently, therefore, it becomes necessary for the patient to adopt a method of ceasing menstruation, namely, to use Gn-RH analog (which suppresses secretion of LH and FSH from the hypophysis to inhibit secretion of estrogens by the ovary, consequently ceasing menstruation). Nevertheless, this treatment very frequently entails the symptoms of ovarian deficiency such as hot flushes and systemic malaise, leading to an impaired quality of life. Moreover, the patient has a recurrence of dysmenorrhea after the completion of the treatment in almost all cases.

The French maritime pine bark extract given produced an analgesic effect greater than is achieved by usual analgesics. The eight cases include three cases wherein the menstrual pain mitigated or disappeared without subsequent oral administration of the extract or other analgesics. This reveals an outstanding therapeutic effect of the extract on dysmenorrhea.

Endometriosis (1) Patients

The patients, 22 females from 24 to 49 years in age, had a severe lower abdominal pain and lumbago continually for the past 6 months or longer during every menstrual period and invariably administered an analgesic (Voltaren, Sedes or the like) as in the foregoing cases of dysmenorrhea. The patients were clinically diagnosed as having endometriosis by gynecological examination, hematological examination (findings as to inflammation, serum CA- 125) and imaging examination (CT scan and MRI).

(2) Method of Administration

The medicinal composition was given to the 22 patients listed in Table 2 by one of the same three methods A, B and C as described for dysmenorrhea, 13 patients by method A, 8 patient by method B and one patient by method C. For a definite diagnosis, histological diagnosis of the lesion with a laparoscope or by celiotomy is most reliable. In the case where the lesion has spread to some extent, however, a rise is observed in serum CA-125, which is one of tumor markers. Accordingly, a significant rise in serum CA- 125 was used as an endometriosis marker in the present invention, and a rise or drop in CA-125 was interpreted as indicating progress or amelioration of the pathological change.

TABLE 2

Treatment for Endometriosis with the Extract

| Patient | Age | Chief complaint | Diagnosis | Method and period | Improvement Mens. cramp | Tenderness |
|---|---|---|---|---|---|---|
| 1 | 38 | Severe cramp | Endometriosis | A x 1 | Marked | — |
| 2 | 37 | Severe cramp | Adenomyosis | A x 1 | No | — |
| 3 | 28 | Severe cramp | Endometriosis | A x 1 | Moderate | No |
| 4 | 41 | Severe cramp | Endometriosis | C x 2 | No | — |
| 5 | 24 | Severe lower abdominal pain | Endometriosis | A x 1 | No | — |
| 6 | 49 | Severe lumbago | Endometriosis | A x 1 | No | — |
| 7 | 30 | Severe cramp | Endometriosis | A x 2 | Marked | Moderate |

TABLE 2-continued

Treatment for Endometriosis with the Extract

| Patient | Age | Chief complaint | Diagnosis | Method and period | Improvement Mens. cramp | Tenderness |
|---|---|---|---|---|---|---|
| 8 | 35 | Severe lumbago | Endometriosis | B x 1 | No | — |
| 9 | 49 | Severe lumbago | Endometriosis | B x 1 | Moderate | Moderate |
| 10 | 29 | Severe cramp | Endometriosis | A x 3 | Marked | — |
| 11 | 24 | Severe cramp | Endometriosis | A x 1 | Slight | — |
| 12 | 28 | Severe cramp | Endo. + myoma | A x 1 | No | — |
| 13 | 34 | Severe cramp | Endo. + myoma | A x 1 | Marked | — |
| 14 | 41 | Severe cramp | Endometriosis | A x 3 | Moderate | Moderate |
| 15 | 24 | Severe cramp | Endometriosis | A x 1 | Marked | — |
| 16 | 41 | Severe cramp | Endometriosis | A x 2 | Greatest | — |
| 17 | 26 | Severe cramp | Endometriosis | B x 1 | Marked | Moderate |
| 18 | 31 | Severe cramp | Endometriosis | B x 1 | Marked | Moderate |
| 19 | 24 | Severe cramp | Endometriosis | B x 1 | Slight | Moderate |
| 20 | 28 | Severe cramp | Endometriosis | B x 1 | No | No |
| 21 | 46 | Severe cramp | Endometriosis | B x 1 | Moderate | Moderate |
| 22 | 21 | Severe cramp | Endometriosis | B x 1 | No | No |

(3) Result

The menstrual pain mitigated or disappeared in 14 cases (63%). When Douglas' cul-de-sc was gynecologically checked for tenderness, an improvement was found in six (60%) of the ten cases of tenderness observed before the administration of the extract. When the patients of six cases, No. 17 to No. 22 of Table 2, were checked for variations in serum CA-125, an apparent reduction was found in serum CA-125 in three cases (50%) as shown in Table 3. Prolongation of menstrual duration (one case) and prolongation of cycles of menstruation (one case) were found as minor side effects.

TABLE 3

Variations in Serum CA-125 of Patients (No. 17–No. 27) Having Endometriosis and Treated with the Extract

| Patient | Method and period | Before treatment | 1 month before treatment | Improvement |
|---|---|---|---|---|
| 17 | B x 1 | 51 | 33 | Moderate |
| 18 | B x 1 | 119 | 13 | Moderate |
| 19 | B x 1 | 45 | 31 | Moderate |
| 20 | B x 1 | 27 | 28 | No |
| 21 | B x 1 | 62 | 56 | No |
| 22 | B x 1 | 56 | 55 | No |

Evaluation

Presently, endometriosis is treated chiefly with Gn-RH analog. This treatment is conducted usually for 6 months, effectively alleviating or eliminating the menstrual pain due to endometriosis and pain due to other causes in the meantime. However, symptoms of ovarian deficiency appear with a high frequency during the treatment, seriously impairing the quality of life. Moreover, the incidence of subsequent recurrence of endometriosis is almost 100% in patients up to 40 years in age.

The menstrual pain was remarkably mitigated or eliminated by the administration of the French maritime pine bark extract for treating endometriosis. Furthermore, an apparent reduction in serum CA-125 was achieved in three cases one month after the administration, this suggesting that the extract has a therapeutic effect on endometriosis, whereas the side effects involved are prolongation of menstrual duration (one case) and prolongation of cycles of menstruation (one case) and are very small. These findings indicate that the extract is more effective on endometriosis than the conventional therapeutic means.

The French maritime pine bark extract comprises dry extracted substances obtained from the bark of a French maritime pine and including living body flavonoids, catechin, taxifolin, phenolic fruit acids and various other proanthocyanidins of different structures. While various animal experiments have substantiated that the extract has antiinflammatory activity (Gabor M. et al., 1993), this antiinflammatory activity is thought attributable to the presence of proanthocyanidins in the extract. Accordingly, it is believed that the effect of the extract to ameliorate or cure dysmenorrhea and endometriosis is produced by the proanthocyanidins.

Besides the proanthocyanidins, the aforementioned caffeic acid and ferulic act very rapidly not only on the entire uteri of rats but also on vascular walls thereof (Ortiz de Urbina et al., Phytotherapy Res. 4: 71–76, 1990). Reportedly, ferulic acid inhibits uterine contraction (Ozaki and Ma, Chem. Pharm. Bull., 38: 1620–1623, 1990). It therefore appears that among other components of the extract, these components also act to alleviate the severe menstrual pain in addition to the proanthocyanidins.

It is further reported that the ability of the extract to remove active oxygen plays an important role for the function of the human endometrium (Sugino et al., Human Rerod 11: 1073–4, 1996). A report is also made on variations of the active oxygen level in the endometrium (Dabrosin et al., J. Clin. Endocrin. Metab 82: 1382–4, 1997). These reports are suggestive of the possibility that the normal human endometrium will be maintained by the active oxygen removal ability of the extract.

ADVANTAGE OF THE INVENTION

The results given in Tables 1 and 2 reveal that the therapeutic composition of the present invention functions very effectively on patients having dysmenorrhea or endometriosis and suffering over a prolonged period of time from menstrual pain on which the conventional medicinal therapies are almost ineffective. This indicates the effectiveness of the composition of the invention.

What is claimed is:

1. A method for relieving the severity of a cramp due to dysmenorrhea, comprising orally administering a composition comprising a plant extract suitable for oral administration, said extract being of a therapeutically effective amount to relieve severity of a cramp caused by dysmenorrhea and being derived from at least one of pine trees, cones of cypress trees and grape seeds.

2. A method for relieving severity of a cramp due to endometriosis, comprising orally administering a plant extract being of a therapeutically effective amount to relieve severity of a caused by endometriosis and being derived from at least one of pine trees, cones of cypress trees and grape seeds.

* * * * *